US00PP33915P2

(12) United States Plant Patent
Trees

(10) Patent No.: US PP33,915 P2
(45) Date of Patent: Jan. 25, 2022

(54) ***MONARDA* PLANT NAMED 'BALBEEMAV'**

(50) Latin Name: *Monarda didyma*
Varietal Denomination: Balbeemav

(71) Applicant: Ball Horticultural Company, West Chicago, IL (US)

(72) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/400,316

(22) Filed: Aug. 12, 2021

(51) Int. Cl.
*A01H 5/02* (2018.01)
*A01H 6/50* (2018.01)

(52) U.S. Cl.
USPC ..... Plt./455

(58) Field of Classification Search
USPC ..... Plt./455
CPC ... A01H 5/02; A01H 5/00; A01H 6/50; A01H 6/504; A01H 6/14
See application file for complete search history.

*Primary Examiner* — June Hwu
(74) *Attorney, Agent, or Firm* — Audrey Charles

(57) ABSTRACT

A new and distinct cultivar of *Monarda* plant named 'Balbeemav', characterized by its medium lavender-colored inflorescences, dark green-colored foliage, good powdery mildew resistance, and moderately vigorous, upright growth habit, is disclosed.

1 Drawing Sheet

Latin name of genus and species of plant claimed: *Monarda didyma.*

Variety denomination: 'Balbeemav'.

BACKGROUND OF THE INVENTION

The present invention relates to a new and distinct cultivar of *Monarda* plant botanically known as *Monarda didyma* and hereinafter referred to by the cultivar name 'Balbeemav'.

The new cultivar originated in a controlled breeding program in Guadalupe, Calif. during the summer 2014. The objective of the breeding program was the development of *Monarda* cultivars that are medium height, early flowering, and have good powdery mildew resistance.

The new *Monarda* cultivar is the result of open-pollination. The female (seed) parent of the new cultivar is the proprietary *Monarda didyma* breeding selection coded 16915, not patented, characterized by its light lavender-colored inflorescences, medium green-colored foliage, and moderately vigorous, compact-upright growth habit. The male (pollen) parent of the new cultivar is unknown. The new cultivar was selected as a single flowering plant within the progeny of the above stated open-pollination during October 2015 in a controlled environment in Guadalupe, Calif.

Asexual reproduction of the new cultivar by terminal stem cuttings since October 2015 in Guadalupe, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balbeemav' as a new and distinct cultivar of *Monarda* plant:

1. Medium lavender-colored inflorescences;
2. Dark green-colored foliage;
3. Good powdery mildew resistance; and
4. Moderately vigorous, upright growth habit.

Plants of the new cultivar differ from plants of the female parent primarily in having darker lavender-colored inflorescences and a taller, upright growth habit.

Of the many commercially available *Monarda* cultivars, the most similar in comparison to the new cultivar is Balmy Lilac 'Balbalmac', U.S. Plant Pat. No. 26,594. However, in side-by-side comparisons, plants of the new cultivar differ from plants of 'Balbalmac' in at least the following characteristics:

1. Plants of the new cultivar have an inflorescence color that is slightly lighter in color than plants of 'Balbalmac';
2. Plants of the new cultivar have shorter-sized bracts than plants of 'Balbalmac'; and
3. Plants of the new cultivar are taller than plants of 'Balbalmac'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balbeemav'. The plants were approximately 5.5 months old. The plants were grown three plants per pot in 1.7 gallon containers for approximately 3 months in an outdoor nursery in West Chicago, Ill. Plants were given two pinches prior to transplant and one pinch one week after transplant.

DETAILED BOTANICAL DESCRIPTION

Figure 1:
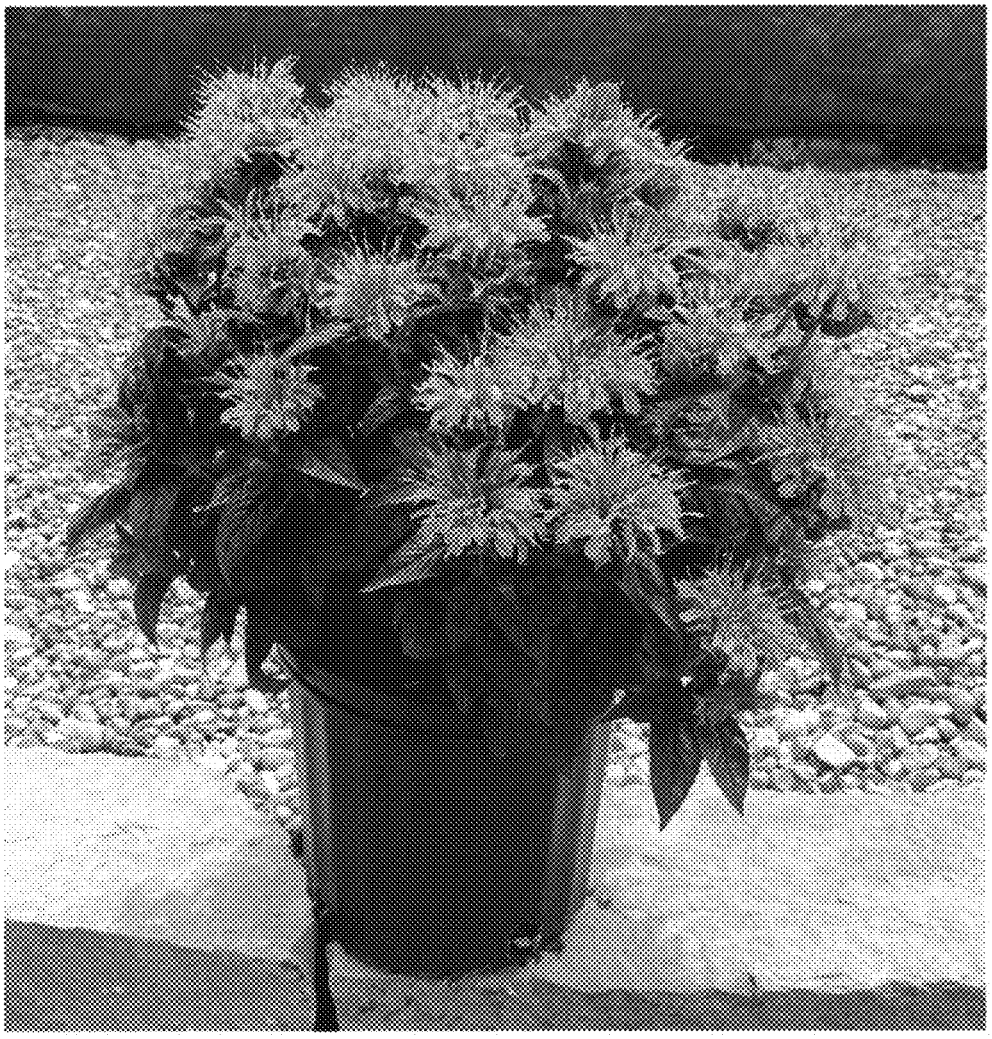
FIG. 1 illustrates a side view of the overall growth and flowering habit of 'Balbeemav'.
Figure 2:
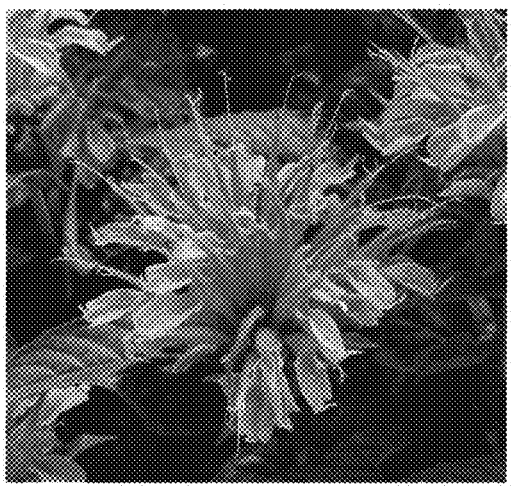
FIG. 2 illustrates a close-up view of an individual inflorescence of 'Balbeemav'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2021 under natural light conditions in Naperville, Ill.

The following descriptions and measurements describe approximately 5.5-month-old plants produced from cuttings from stock plants and grown under conditions comparable to those used in commercial practice. The plants were grown three plants per pot in 1.7 gallon containers for approximately 3 months in an outdoor nursery in West Chicago, Ill. Plants were given two pinches prior to transplant and one pinch one week after transplant. Prior to transplant plants were grown in liners in a poly-covered greenhouse in West Chicago, Ill. Greenhouse temperatures ranged from an average high of 79.5° F. (26.4° C.) to an average low of 68.5° F. (20.3° C.), and supplemental lighting was provided daily for five hours during short days. Measurements and numerical values represent averages of typical plant.

Botanical classification: *Monarda didyma* 'Balbeemav'.

Parentage:

*Female parent.*—Proprietary *Monarda didyma* breeding selection coded 16915, not patented.

*Male parent.*—Unknown.

Propagation:

*Type cutting.*—Terminal stem.

*Time to initiate roots.*—Approximately 7 to 10 days.

*Time to produce a rooted cutting.*—Approximately 35 to 42 days.

*Root description.*—Fine, fibrous.

*Rooting habit.*—Freely branching.

Plant description:

*Commercial crop time.*—Approximately 9 to 11 weeks from a rooted cutting to finish in a 15 cm pot.

*Growth habit and general appearance.*—Herbaceous perennial, moderately vigorous, upright growth habit.

*Hardiness.*—USDA Zone 4 (−30° F. to −20° F./−34.4° C. to −28.9° C.).

*Size.*—Height from soil level to top of plant plane: Approximately 29.0 cm. Width: Approximately 40.0 cm.

*Branching habit.*—Freely branching. Pinching enhances lateral branching. Quantity of main branches per plant: Approximately 4.

*Branch.*—Shape: Square in cross section. Strength: Strong. Length to base of inflorescence: Approximately 20.0 cm. Diameter: Approximately 4.0 mm to 6.0 mm. Length of central internode: Approximately 3.1 cm. Texture: Densely pubescent on edges. Color of young stems: 146C. Color of mature stems: 146B, becoming woody 200B with age.

Foliage description:

*General description.*—Quantity of leaves per branch: Approximately 8. Fragrance: Strong, sage-like. Form: Simple. Arrangement: Opposite, decussate.

*Leaves.*—Aspect: Primarily perpendicular to stem. Shape: Ovate to lanceolate. Margin: Serrate. Apex: Acute. Base: Shallowly cordate. Venation pattern: Pinnate. Length of mature leaf: Approximately 6.5 cm. Width of mature leaf: Approximately 3.4 cm. Texture of upper surface: Slightly rugose, moderately pubescent. Texture of lower surface: Densely pubescent. Color of upper surface of young and mature foliage: Closest to NN137A with venation of 146B. Color of lower surface of young and mature foliage: Closest to 137C with venation of 146D.

*Petiole.*—Length: Approximately 6.0 mm. Diameter: Approximately 3.0 mm. Texture: Densely pubescent. Color: 146D.

Flowering description:

*Flowering habit.*—'Balbeemav' is a long-day obligate, vernalization is not required for flowering, freely flowering under outdoor growing conditions blooming late spring through summer.

*Lastingness of individual flower.*—Approximately 5 to 7 days.

Inflorescence description:

*General description.*—Type: Dense terminal verticillasters, not persistent, facing upward and outward.

*Quantity of inflorescences per plant.*—Approximately 17. Fragrance: Strong, sage-like. Depth or height of inflorescence: Approximately 4.0 cm. Width of inflorescence: Approximately 5.5 cm, expands to approximately 7.0 cm as innermost flowers senesce. Quantity of fully-open flowers per inflorescence: Approximately 42.

*Peduncle.*—Shape: Square in cross section. Strength: Strong. Aspect: Erect. Length: Approximately 4.0 cm. Diameter: Approximately 3.0 mm. Texture: Densely pubescent on edges. Color: 146B.

Flower description:

*Type.*—Single, bilabiate.

*Bud.*—Rate of opening: Generally takes 2 to 3 days for bud to progress from first color to fully open flower.

*Bud just before opening.*—Shape: Tubular, upper portion strongly curved downward. Length: Approximately 1.4 cm. Diameter: Approximately 2.0 mm. Texture: Densely pubescent. Color: N80C.

*Corolla.*—Shape: Two lips, upper lip hooded; lower lip, a single lobe; lips fused. Depth (height): Approximately 3.9 cm. Width: Approximately 5.0 mm. Length: Approximately 1.3 cm.

*Upper lip.*—Shape: Linear, hooded. Aspect: Erect. Margin: Entire. Apex: Two acute tips. Length: Approximately 1.1 cm. Width: Approximately 1.0 mm. Texture of inner surface: Glabrous. Texture of outer surface: Densely pubescent. Color of inner surface when first and fully open: N80C. Color of outer surface when first and fully open: N80A, fading to N80D with senescence.

*Lower lip.*—Shape: Oblanceolate. Margin: Entire. Apex: Curled lobe at apex about 4.0 mm in length and 1.0 mm in width. Length: Approximately 1.3 cm. Width: Approximately 5.0 mm. Texture of upper surface: Glabrous. Texture of lower surface: Densely pubescent. Color of upper surface when first and fully open: N80C, fading to lighter than N80D with senescence. Color of lower surface when first and fully open: Between N80B and N80C, fading to lighter than N80D with senescence.

*Corolla tube.*—Length: Approximately 1.9 cm. Width: Approximately 2.0 mm. Texture of inner surface: Sparsely pubescent. Texture of outer surface: Densely pubescent. Color: N80A to N80B, fading to N80D with senescence.

*Calyx.*—Shape: Tubular. Length: Approximately 1.0 cm. Diameter: Approximately 2.0 mm.

*Sepals.*—Quantity per flower: 5, fused except for acuminate apex of 1.0 mm in length having an entire margin. Length: Approximately 1.0 cm. Width: Less than 1.0 mm. Texture of inner surface: Glabrous. Texture of outer surface: Densely pubescent. Color of inner surface: 145B with N186A on tips. Color of outer surface: 145A with N186A on tips.

*Bracts.*—Quantity: Approximately 28 per inflorescence in multiple whorls. Shape: Ovate to lanceolate. Length of larger: Approximately 3.5 cm. Width of larger: Approximately 1.8 cm. Length of smaller: Approximately 9.0 mm. Width of smaller: Less than 1.0 mm. Texture of upper and lower surfaces: Densely pubescent. Color of upper surface of larger bracts: Closest to NN137A with center of base of 137D. Color of lower surface of larger bracts: 137B. Color of upper and lower surfaces of smaller bracts: 146C.

*Reproductive organs.*—Androecium: Stamen quantity: 2 per flower, dorsifixed. Filament length: Approximately 3.4 cm. Filament length of fixed portion: Approximately 1.9 cm. Filament color: NN155D with an overlay of 83C near anther. Anther shape: Narrowly elliptic to oblong. Anther length: Approximately 2.0 mm. Anther color: 83B. Pollen amount: Moderate. Pollen color: NN155D. Gynoecium: Pistil quantity: 1 per flower. Pistil length: Approximately 3.9 cm. Stigma shape: Cleft, two-parted. Stigma length: Approximately 2.0 mm. Stigma color: 90A. Style length: Approximately 3.6 cm. Style color: NN155D, opaque with an overlay of 90A near stigma. Ovary length: Approximately 1.0 mm. Ovary color: 155A.

Seed and fruit production: Neither seed nor fruit production has been observed.

Disease and pest resistance: Good resistance to powdery mildew has been observed.

What is claimed is:

1. A new and distinct cultivar of *Monarda* plant named 'Balbeemav', substantially as herein illustrated and described.

* * * * *